(12) United States Patent
Mouchawar et al.

(10) Patent No.: US 6,321,115 B1
(45) Date of Patent: Nov. 20, 2001

(54) NOISE DETECTION SYSTEM AND METHOD FOR USE IN AN IMPLANTABLE MEDICAL DEVICE

(75) Inventors: Gabriel A. Mouchawar, Newhall; James D. Causey, III, Simi Valley; Wayne A. Morgan, Northridge; Mae-Mae Shieh, Palo Alto; Curtis A. Knight, Sunnyvale, all of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/453,654

(22) Filed: Dec. 3, 1999

(51) Int. Cl.[7] .................................................. A61N 1/362
(52) U.S. Cl. ............................................................ 607/9
(58) Field of Search ........................ 607/9, 27; 600/509, 600/510, 300; 128/901

(56) References Cited

U.S. PATENT DOCUMENTS

| | | |
|---|---|---|
| 4,173,230 | 11/1979 | Digby . |
| 4,386,610 | 6/1983 | Leckrone . |
| 4,432,362 | 2/1984 | Leckrone te al. . |
| 4,545,380 | 10/1985 | Schroeppel . |
| 4,712,555 | 12/1987 | Thornander et al. . |
| 4,788,980 | 12/1988 | Mann et al. . |
| 4,940,052 | 7/1990 | Mann et al. . |
| 4,944,298 | 7/1990 | Sholder . |
| 5,010,887 | 4/1991 | Thornander . |
| 5,702,425 | 12/1997 | Wickham ................................ 607/9 |
| 5,766,227 | 6/1998 | Nappholz et al. ........................ 607/9 |

*Primary Examiner*—Scott M. Getzow (57) ABSTRACT

An implantable cardiac stimulation device includes a system for detecting noise in an electrogram signal. The system for detecting noise generates an event signal when the electrogram signal exceeds a threshold. A timer times a refractory time period responsive to an event signal. During the refractory time period, a zero crossing detector generates a zero crossing signal when the electrogram signal transitions between positive and negative values. A counter counts the zero crossing signals during the time period and a comparator determines if the counter reached a predetermined count during the time period. If the counter exceeds a programmable count, a noise detection flag is set and the controller is alerted to the presence of noise in its input signal.

43 Claims, 7 Drawing Sheets

NOISE DETECTION SYSTEM AND METHOD FOR USE IN AN IMPLANTABLE MEDICAL DEVICE

FIELD OF THE INVENTION

The present invention is generally directed to an implantable medical device, e.g., a cardiac stimulation device and is particularly directed to a noise detection system and method for use in such a device.

BACKGROUND OF THE INVENTION

Implantable cardiac stimulation devices are well known in the art. They include implantable pacemakers which provide stimulation pulses to cause a heart, which would normally or otherwise beat too slowly or at an irregular rate, to beat at a controlled normal rate. They also include defibrillators which detect when the atria and/or the ventricles of the heart are in fibrillation and apply cardioverting or defibrillating electrical energy to the heart to restore the heart to a normal rhythm. Implantable cardiac stimulation devices may also include the combined functionalities of a pacemaker and a defibrillator.

As is well known, implantable cardiac stimulation devices sense cardiac activity for monitoring the cardiac condition of the patient in which the device is implanted. By sensing the cardiac activity of the patient, the device is able to provide cardiac stimulation therapy when it is required.

Unfortunately, noise within the sensing channel bandwidth can interfere with the sensing function. In a pacemaker, for example, noise can be mistaken by the device for a legitimate cardiac event causing stimulation inhibition. This can lead to long periods of asystole. In an implantable defibrillator, noise can cause mistaken diagnosis of fibrillation resulting in inappropriate therapy delivery.

Common sources of noise are either external, such as power line noise, or internal, such as noise from muscle activation. These sources present a particular problem because they generally pass through the sensing bandpass filter with little or no attenuation.

Noise detection systems for use in implantable cardiac stimulation devices are known in the art. However, prior art noise detection systems generally contemplate the use of long refractory periods wherein cardiac events occurring during the refractory period are not acted upon by the device because of the refractory period extension. This can cause the devices in which such prior art noise detection systems are employed to miss normal activations or cardiac events which occur simultaneously with the noise. The present invention addresses this and other deficiencies of prior art noise detection systems.

SUMMARY OF THE INVENTION

The present invention provides a system for detecting noise in an electrogram signal generated by an implantable cardiac stimulation device. The noise detection system includes a threshold circuit that generates an event signal when the electrogram signal exceeds a threshold, a timer that times a time period responsive to an event signal, and a zero crossing detector that generates a zero crossing signal when the electrogram signal transitions between positive and negative values. The noise detection system further includes a counter that counts the zero crossing signals during the time period and a comparator that determines if the counter reaches a predetermined count during the time period. When the comparator determines that the zero crossings in the electrogram signal exceed a predetermined number of zero crossings during the time period, the detection of noise is declared and the device ignores the event signal as a legitimate cardiac event.

Zero crossing detection, in accordance with one embodiment of the present invention, may be accomplished by noting sign changes in the electrogram signal. Alternatively, the zero crossing detection may be accomplished by detecting when the electrogram signal transitions from above a positive threshold to below a negative threshold or from below the negative threshold to above the positive threshold.

In accordance with other aspects of the present invention, the noise detection time period initiated upon the electrogram signal exceeding a threshold may be on the order of 90 to 250 milliseconds. Further, the noise detection time period may be a refractory period comprising first and second refractory period portions of equal duration. In accordance with this embodiment of the present invention, noise detection is declared when the number of zero crossings occurring during each of the first and second refractory period portions is greater than a predetermined number of zero crossings.

The present invention further provides a method of detecting noise in an electrogram signal for use in an implantable cardiac stimulation device. The method includes the steps of generating an event signal when the electrogram signal exceeds a threshold, detecting zero crossings in the electrogram signal during a time period following an event signal, and determining if the zero crossings in the electrogram signal exceed a predetermined number of zero crossings during the time period.

BRIEF DESCRIPTION OF THE DRAWINGS

The above and other aspects, features and advantages of the present invention will be apparent from the following more particular description thereof, presented in conjunction with the accompanying drawings wherein.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention may be used with various types of implantable stimulation devices, including an implantable pacemaker configured to treat bradycardia and/or tachycardia, an implantable cardioverter/defibrillator (ICD), or a combination thereof.

To better understand the invention, it will first be helpful to have an understanding of the basic functions performed by the implantable stimulation device with which the invention is used, e.g., an ICD device and/or a dual-chamber pacemaker. While a dual-chamber device has been chosen, this is for teaching purposes only. It is recognized that the present invention could be implemented in a single-chamber device, that one of skill in the art could readily adapt the dual-chamber device shown in FIG. 2 to perform single-chamber functionality, and that a single-chamber device is within the spirit of the invention.

Figure 1:
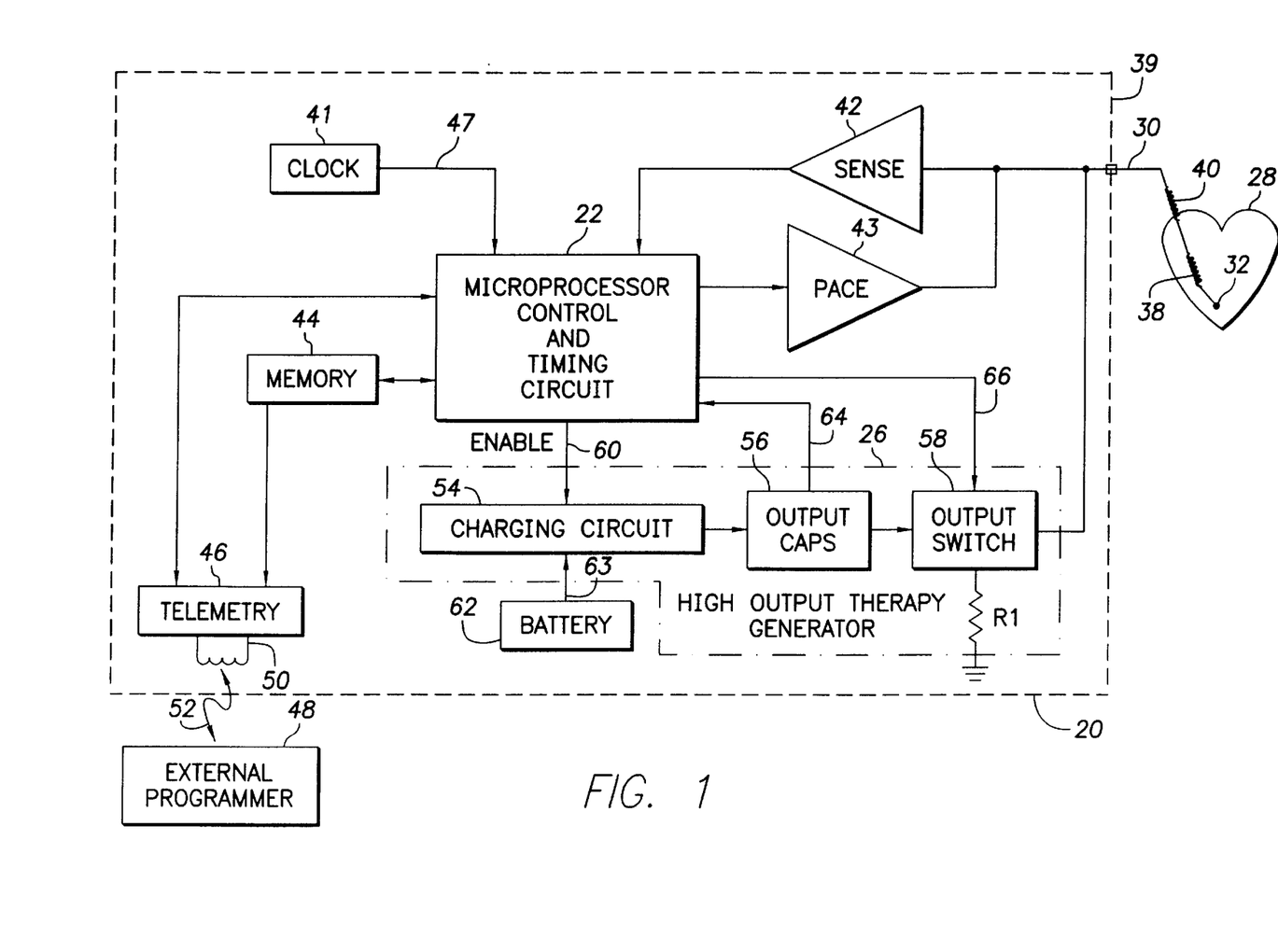
FIG. 1 shows a simplified functional block diagram of an implantable cardioverter/defibrillator (ICD), which represents one type of implantable cardiac stimulation device with which the present invention may be used.
Figure 2:
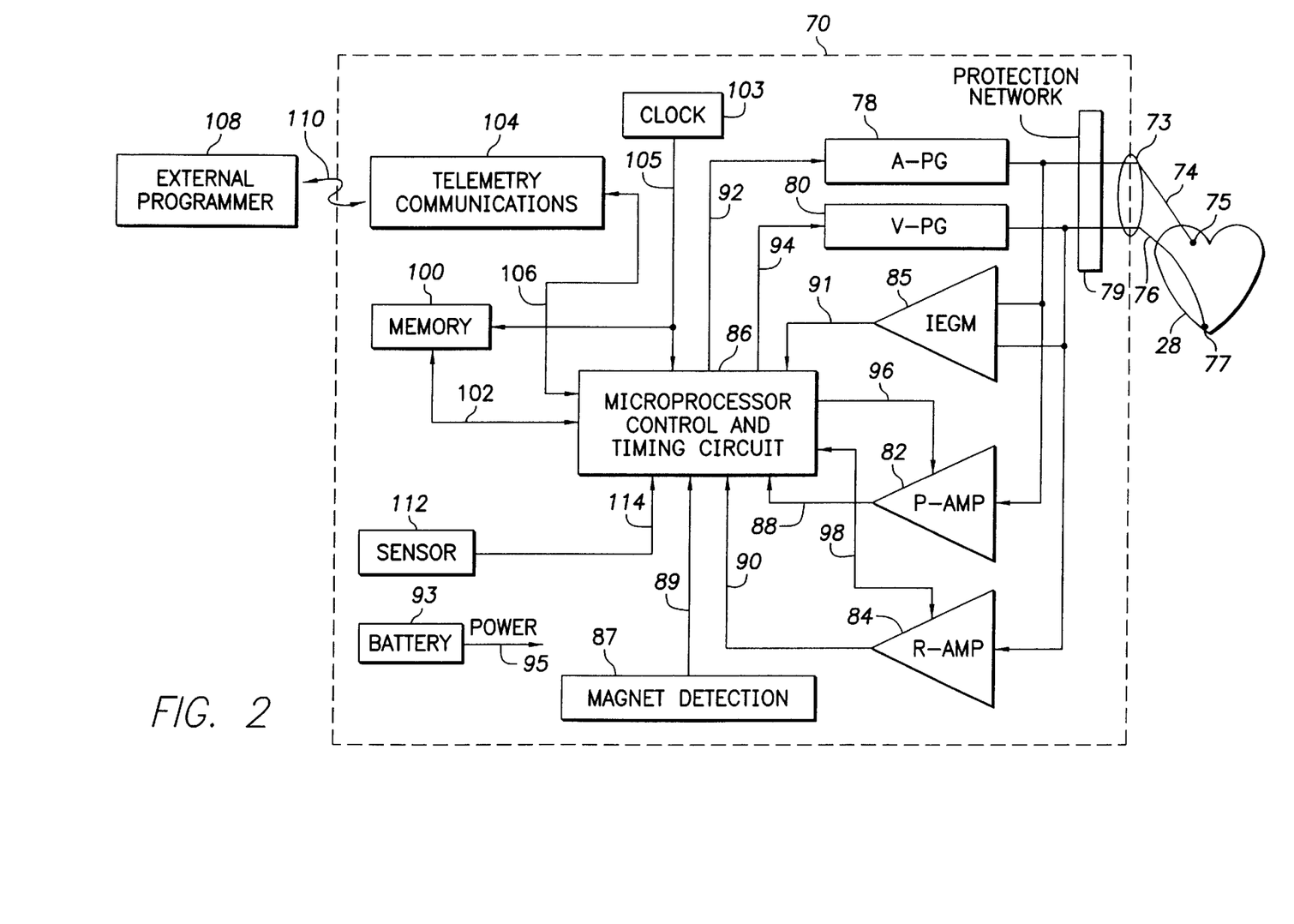
FIG. 2 shows a functional block diagram of an implantable dual-chamber pacemaker, which represents another type of implantable medical device with which the invention may be used.

In FIG. 1, there is shown a simplified functional block diagram of an ICD device 20, and in FIG. 2, there is shown a simplified functional block diagram of a dual-chamber pacemaker 70. It should also be noted that in some instances the functions of an ICD and a pacemaker may be combined within the same stimulation device. However, for teaching purposes, the devices will be described as separate stimulation devices.

It is the primary function of an ICD device to sense the occurrence of an arrhythmia, and to automatically apply an appropriate electrical shock therapy to the heart aimed at terminating the arrhythmia. To this end, the ICD device 20 as shown in the functional block diagram of FIG. 1, includes a microprocessor control and timing circuit (hereinafter referred to as a control/timing circuit) 22, such as a microprocessor, state machine or other such control circuitry, that controls a high output therapy generator 26. The high output therapy generator 26 generates electrical stimulation pulses of moderate or high energy (corresponding to cardioversion or defibrillation pulses, respectively), e.g., electrical pulses having energies of from 1–10 joules (moderate), or 11–40 joules (high), as controlled by the control/timing circuit 22.

Such moderate or high energy pulses are applied to the patient's heart 28 through at least one lead 30 having at least one defibrillation electrodes, such as coil electrode 38 used in conjunction with the casing 39 of the ICD or pacemaker. The lead 30 preferably also includes at least one electrode for pacing and sensing functions, such as electrode 32. Typically, the lead 30 is transvenously inserted into the heart 28 so as to place the coil electrode 38 in the apex of the heart 28 and electrode 40 in the superior vena cava, respectively. While only one lead is shown in FIG. 1, it is to be understood that additional defibrillation leads and electrodes may be used as desired or needed in order to efficiently and effectively apply the shock treatment generated by the high output therapy generator 26 to the patient's heart 28.

The ICD 20 also includes a sense amplifier 42 that is coupled to at least one sensing electrode 32. It is the function of the sense amplifier 42 to sense the electrical activity of the heart 28, as is known in the art, to generate an electrogram including R-waves which occur upon depolarization, and hence contraction, of ventricular tissue; and P-waves which occur upon the depolarization, and hence contraction, of atrial tissue. Thus by sensing R-waves and/or P-waves through the sense amplifier 42, and by providing the control/timing circuit 22 with the generated electrogram, the control/timing circuit 22 is able to make a determination as to the rate and regularity of the patient's heartbeat. Such information, in turn, allows the control/timing circuit 22 to determine whether the patient's heart 28 of a patient is experiencing an arrhythmia, and to apply appropriate stimulation therapy.

The control/timing circuit 22 further has a memory circuit 44 coupled thereto wherein the operating parameters used by the control/timing circuit 22 are stored. Such operating parameters define, for example, the amplitude of each shock energy pulse to be delivered to the patient's heart 28 within each tier of therapy, as well as the duration of these shock pulses. The memory 44 may take many forms, and may be subdivided into as many different memory blocks or sections (addresses) as needed to store desired data and control information.

Advantageously, the operating parameters of the ICD 20 may be non-invasively programmed into the memory 44 through a telemetry circuit 46, in telecommunicative contact with an external programmer 48 by way of a suitable coupling coil 50. The coupling coil may serve as an antenna for establishing a radio frequency (RF) communication link 52 with the external programmer 48; or the coil 50 may serve as a means for inductively coupling data between the telemetry circuit 46 and the external programmer 48, as is known in the art. Further, such telemetry circuit 46 advantageously allows status information relating to the operation of the ICD 20 as contained in the control/timing circuit 22 or memory 44, to be sent to the external programmer 48 through the established link 52.

The control/timing circuit 22 includes appropriate processing and logic circuits for analyzing the electrogram generated by the sense amplifier 42 and determining if such signals indicate the presence of an arrhythmia. Typically, the control/timing circuit 22 is based on a microprocessor, or similar processing circuit, which includes the ability to process or monitor input signals (data) in a prescribed manner, e.g., as controlled by program code stored in a designated area or block of the memory 44. The details of the design and operation of the control/timing circuit 22 are not critical to the present invention. Rather, any suitable control/timing circuit 22 may be used that carries out the functions described herein. The use, design, and operation of microprocessor-based control circuits to perform timing and data analyses functions is known in the art.

A clock circuit 41 directs an appropriate clock signal to the control/timing circuit 22, as well as to any other needed circuits throughout the ICD 20, e.g., to the memory 44, by way of clock bus 47.

The ICD 20 additionally includes a battery 62. The battery 62 provides operating power to all of the circuits of the ICD 20 via a POWER signal line 63.

In FIG. 2, a simplified block diagram of the circuitry needed for a dual-chamber pacemaker 70 is illustrated. The pacemaker 70 is coupled to the patient's heart 28 by way of leads 74 and 76, the lead 74 having an electrode 75 that is in contact with one of the atria of the heart 28, and the lead 76 having an electrode 77 that is in contact with one of the ventricles of the heart 28. The leads 74 and 76 are electrically and physically connected to the pacemaker 70 through a connector 73 that forms an integral part of the housing wherein the circuits of the pacemaker 70 are housed.

The connector 73 is electrically connected to a protection network 79, which network 79 electrically protects the circuits within the pacemaker 70 from excessive shocks or voltages that could appear on the electrodes 75 and/or 77 in the event such electrodes were to come in contact with the high voltage signal, e.g., from a defibrillation shock.

The leads 74 and 76 carry stimulation pulses to electrodes 75 and 77 from an atrial pulse generator (A-PG) 78 and a ventricular pulse generator (V-PG) 80, respectively. Further, electrical signals from the atria are carried from the electrode 75 through the lead 74, to the input terminal of an atrial channel sense amplifier (P-AMP) 82 and electrical signals from the ventricles are carried from the electrode 77 through the lead 76 to the input terminal of a ventricular channel sense amplifier (R-AMP) 84. Similarly, electrical signals from both the atria and ventricles are applied to the inputs of an IEGM (intracardiac electrogram) amplifier 85. The amplifier 85 is typically configured to detect an evoked response from the heart 28 in response to an applied stimulus, thereby aiding in the detection of "capture". (Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue.)

The dual-chamber pacemaker 70 is controlled by a microprocessor control and timing circuit (hereinafter referred to as a control/timing circuit) 86 that typically includes a microprocessor programmed to carry out control and timing functions. The control/timing circuit 86 receives the atrial electrogram signal from the atrial amplifier 82 over signal line 88. Similarly, the control/timing circuit 86 receives the ventricular electrogram signal from the ventricular amplifier 84 over signal line 90, and the output signals from the IEGM amplifier 85 over signal line 91. The control/timing circuit 86 also generates trigger signals that are sent to the atrial pulse generator 78 and the ventricular pulse generator 80 over signal lines 92 and 94, respectively. These trigger signals are generated each time that a stimulation pulse is to be generated by the respective pulse generator 78 or 80. The atrial trigger signal 92 is referred to simply as the "A-trigger" and the ventricular trigger signal 94 is referred to as the "V-trigger".

During the time that either an A-pulse or V-pulse is being delivered to the heart, the corresponding amplifier 82 and/or 84 is typically disabled by way of a blanking signal presented to these amplifiers from the control system over signal lines 96 and 98, respectively. This blanking action prevents the amplifiers 82 and 84 from being saturated from the relatively large stimulation pulses that are present at their input terminals during this time. This blanking action also helps prevent residual electrical signals present in the muscle tissue as a result of the pacemaker stimulation being interpreted as P-waves or R-waves or cross talk which is detected on the R-wave due to an A-pulse or P-wave due to a V-pulse.

As shown in FIG. 2, the pacemaker 70 further includes a memory circuit 100 that is coupled to the control/timing circuit 86 over a suitable data/address bus 102. This memory circuit 100 allows certain control parameters, used by the control/timing circuit 86 in controlling the operation of the pacemaker, to be programmably stored and modified, as required, in order to customize the pacemaker's operation to suit the needs of a particular patient. Further, data sensed during the operation of the pacemaker may be stored in the memory 100 for later retrieval and analysis.

As with the memory 44 of the ICD device 20 shown in FIG. 1, the memory 100 of the pacemaker 70 (FIG. 2) may take many forms, and may be subdivided into as many different memory blocks or sections (addresses) as needed in order to allow desired data and control information to be stored. Preferably, the memory 100 is capable of storing a relatively large amount of sensed data as a data record, which data record may then be used to guide the operation of the device. That is, the operating mode of the pacemaker may be made dependent, at least in part, on past performance data. For example, an average atrial rate may be determined based on the sensed atrial rate over a prescribed period of time. This average rate may then be stored and updated at regular intervals. Such stored rate may then be compared to a present atrial rate and, depending upon the difference, used to control the operating mode of the pacemaker. Other parameters, of course, in addition to (or in lieu of) atrial rate, may be similarly sensed, stored, averaged (or otherwise processed), and then used for comparison purposes against one or more currently sensed parameters. Advantageously, modern memory devices allow for the storage of large amounts of data in this manner.

A clock circuit 103 directs an appropriate clock signal to the control/timing circuit 86, as well as to any other needed circuits throughout the pacemaker 70, e.g., to the memory 100, by way of clock bus 105.

A telemetry/communications circuit 104 is further included in the pacemaker 70. This telemetry circuit 104 is connected to the control/timing circuit 86 by way of a suitable command/data bus 106. In turn, the telemetry circuit 104, which is included within the implantable pacemaker 70, may be selectively coupled to an external programming device 108 by means of an appropriate communication link 110, which communication link 110 may be any suitable electromagnetic link, such as an RF (radio frequency) channel, a magnetic link, an optical link, and the like. Advantageously, through the external program 108 and the communication link 110, desired commands may be sent to the control/timing circuit 86. Similarly, through this communication link 110 with the programmer 108 data commands, either held within the control/timing circuit 86, as in a data latch, or stored within the memory 100, may be remotely received from the programmer 108. Similarly, data initially sensed through the lead 74 or 76 and processed by the microprocessor control circuit 86, or other data measured within or by the pacemaker 70, may be stored and uploaded to the programmer 108. In this manner, non-invasive communications can be established with the implanted pacemaker from a remote, non-implanted location.

The pacemaker 70 additionally includes a battery 93. The battery 93 provides operating power to all of the circuits of the pacemaker 70 via a POWER signal line 95.

It is noted that the pacemaker 70 in FIG. 2 is referred to as a dual-chamber pacemaker because it interfaces with both the atria and the ventricles of the heart. Those portions of the pacemaker 70 that interface with the atria, e.g., the lead 74, the atrial pulse generator 78, and corresponding portions of the control/timing circuit 86, are commonly referred to as the "atrial channel". Similarly, those portions of the pacemaker 70 that interface with the ventricles, e.g., the lead 76, the ventricular sense amplifier 84, the ventricular pulse generator 80, and corresponding portions of the control/timing circuit 86, are commonly referred to as the "ventricular channel".

As needed for certain applications, the pacemaker 70 may further include at least one sensor 112 that is connected to the control/timing circuit 86 of the pacemaker 70 over a suitable connection line 114. While this sensor 112 is illustrated in FIG. 2 as being included within the pacemaker 70, it is to be understood that the sensor may also be external (not shown) to the pacemaker 70, yet still be implanted within or carried by the patient. A common type of sensor is an activity sensor, such as a piezoelectric crystal, that is mounted to the case of the pacemaker 70. Other types of sensors are also known, such as sensors that sense the oxygen content of blood, respiration rate, pH of blood, body motion, and the like. The type of sensor used is not critical to the present invention.

The pacemaker 70 further includes magnet detection circuitry 87, coupled to the control/timing circuit 86 over signal line 89. It is the purpose of the magnet detection circuitry 87 to detect when a magnet is placed over the pacemaker, which magnet may be used by a physician or other medical personnel to perform various reset functions of the pacemaker 70 and/or to signal the control/timing circuit 86 that the external programmer 108 is in place to receive data from, or send data to, the pacemaker memory 100 or control/timing circuit 86 through the telemetry communications circuit 104.

As with the ICD device 20 of FIG. 1, the telemetry or communications circuit 104 may be of conventional design. Similarly, the external programmer 108 may be of any suitable design in the art. Likewise, the memory circuit 100 and the circuits utilized in the atrial and ventricular channels may all be of common design as is known in the pacing art. The present invention is not concerned with the details of the circuitry utilized for each of these pacing elements. Rather, it is concerned with the manner in which all of these pacing elements cooperate with each other in order to provide a particular pacing mode of operation. Such cooperation is controlled by the control/timing circuit 86.

The control/timing circuit 86 may be realized using a variety of different techniques and/or circuits. The preferred type of control/timing circuit 86 is a microprocessor-based control system. It is noted, however, that the control/timing circuit 86 could also be realized using a state machine. Indeed, any type of control circuit or system could be employed for the control/timing circuit 86. The present invention is likewise not concerned with the details of the control/timing circuits 22 and 86. Rather it is concerned with the end result achieved by the control system. That is, so long as the control/timing circuit 86 controls the operation of the pacemaker (or other medical device) so that the desired functions are achieved as set forth herein, e.g., by following the steps described below in the flow charts of FIGS. 4 and 5, it matters little what type of control system is used. Those of skill in the implantable medical device art, given the teachings presented herein, should thus be able to fashion numerous different types of control systems or circuits that achieve the desired device control.

Representative of the type of control systems that may be used with the invention is the microprocessor-based control system described in U.S. Pat. No. 4,940,052 entitled "MICROPROCESSOR CONTROLLED RATE-RESPONSIVE PACEMAKER HAVING AUTOMATIC RATE RESPONSE THRESHOLD ADJUSTMENT". Reference is also made to U.S. Pat. Nos. 4,712,555 and 4,944,298, wherein a state machine type of operation for a pacemaker is described and U.S. Pat. No. 4,788,980 wherein the various timing intervals used within the pacemaker and their inter-relationship are more thoroughly described. The '052, '555, '298, and '980 patents are incorporated herein by reference.

Figure 3:
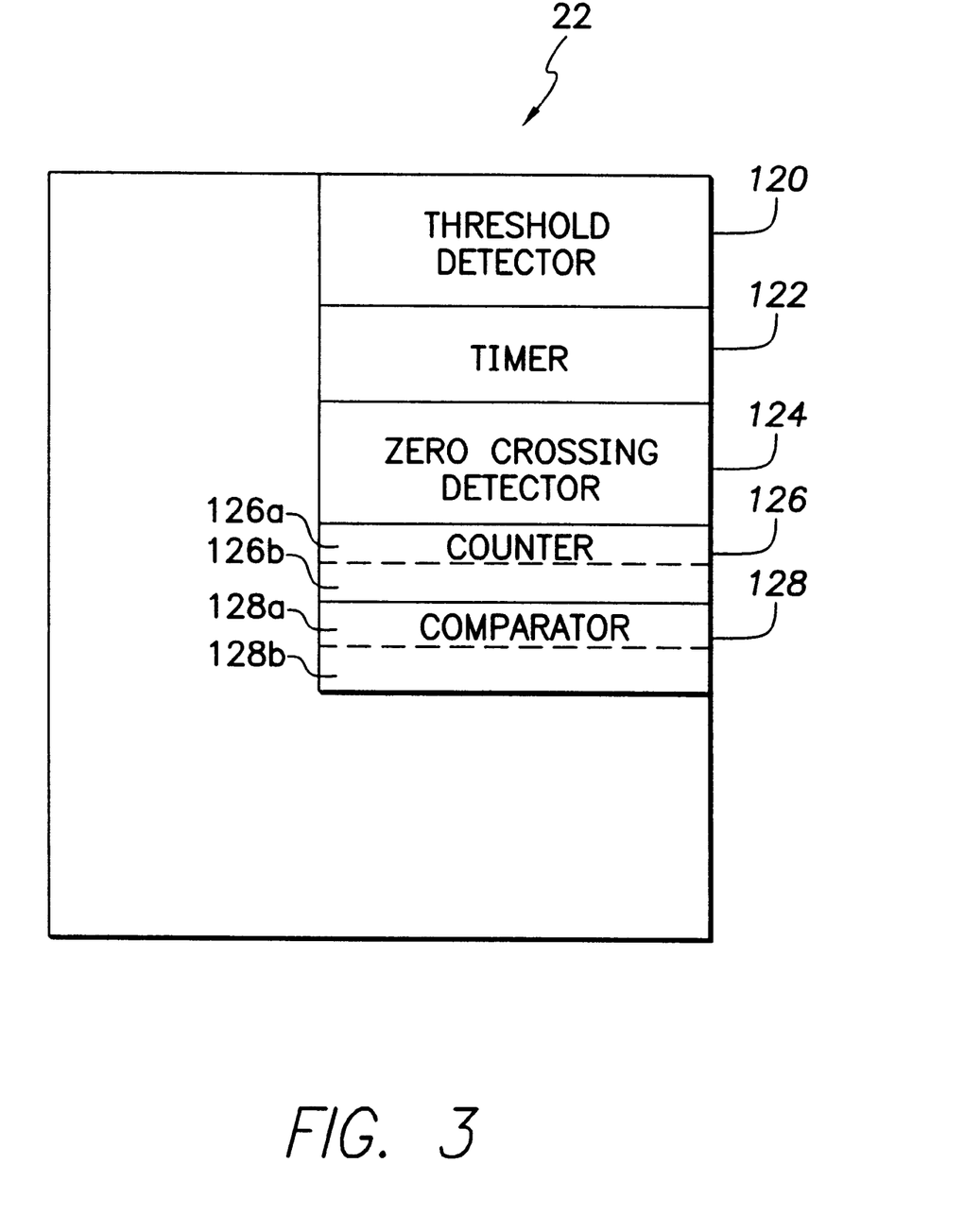
FIG. 3 is a functional block diagram of the functional stages or circuits implemented by a microprocessor in practicing the present invention.

FIG. 3 shows a more detailed representation of the microprocessor control and timing circuit (control/timing circuit) 22 of FIG. 1. More specifically, FIG. 3 shows those functional stages and circuits which the control/timing circuit 22 implements in practicing one embodiment of the present invention. Although the control/timing circuit 22 of FIG.1 is illustrated in FIG. 3, it will appreciated by those skilled in the art that the depiction of FIG. 3 applies equally as well to the control/timing circuit 86 of FIG. 2 for implementing the invention in an implantable pacemaker.

The control/timing circuit 22 includes a threshold circuit 120, a timer circuit 122, a zero crossings detection circuit 124, a counter circuit 126, and a comparator circuit 128. While the function of the circuits will be primarily described with respect to the detection of noise in a ventricular channel, the principles of the present invention also apply with equal applicability to the sensing of noise in an atrial channel.

The threshold circuit 120 sets a threshold for detecting a cardiac event in the ventricular electrogram provided by the sense amplifier 42 of FIG. 1. When the amplitude of the electrogram exceeds the threshold, the threshold circuit 120 generates an event signal.

The event signal from the threshold circuit 120 causes the timer circuit 122 to begin timing a refractory time period. The refractory time period may be, for example, between 90 and 250 milliseconds and is preferably approximately 125 milliseconds. This refractory period is relatively short compared to prior art noise detection arrangements. However, noise detection in accordance with the present invention enables noise detection with such a short refractory period while the shortness of the refractory period assures that legitimate events will not be missed. This permits the implantable device in which the noise detection system of the present invention is employed to accurately diagnose the patient's condition and respond quickly with appropriate therapy.

During the refractory period timed by the timer circuit 122, the zero crossing detection circuit 124 detects zero crossings in the electrogram signal provided by sense amplifier 42. One particular implementation of the zero crossing detection circuit 124 will be described subsequently with respect to FIG. 5. However, other implementations are possible. For example, one preferred way to detect zero crossings is to configure the zero crossing detection circuit 124 to establish a positive and a negative threshold of equal magnitude. A zero crossing is then detected when the electrogram signal transitions from above the positive threshold to below the negative threshold or transitions from below the negative threshold to above the positive threshold. Upon the detection of each such zero crossing transition, zero crossing detector circuit 124 generates a zero crossing signal.

The counter circuit 126 is incremented by each zero crossing signal generated by the zero crossing detection circuit 124. At the end of the refractory period, the counter circuit 126 will contain the number of zero crossings in the electrogram signal occurring during the refractory period.

Upon completion of the timing of the refractory period by the timer circuit 122, the comparator circuit 128 then compares the number of zero crossings in the electrogram signal occurring during the refractory period (the count in counter circuit 126) to a predetermined count. If the comparator circuit 128 determines that the count is greater than a predetermined count, the detection of noise will be declared. This will cause a flag to be set in the control/timing circuit 22. The flag causes the control/timing circuit 22 to ignore the event, which initiated the noise detection, as a legitimate event and also causes a noise reversion mode in the ICD or pacemaker. However, if the comparator circuit 128 determines that the count in counter circuit 126 is less than the predetermined number or count, the event that initiated the noise detection is treated by the control/timing circuit 22 as a legitimate event and also clears the noise reversion mode of the ICD or pacemaker. The event detection will then be used by the implanted device in diagnosing the condition of the patient and determining the need for treatment.

The value of the predetermined count may be determined, for example, by multiplying the product of the minimum frequency of the noise to be detected and the noise detection refractory period by two. As an example, it is assumed that the length of the refractory period is 125 milliseconds or 0.125 seconds. It is also assumed that the minimum frequency of the noise to be detected is 40 Hz (counts/second). The value of the predetermined count is therefore equal to 10 counts, i.e., 0.125 seconds*40 counts/second*2. Therefore, if it is determined by the comparator circuit 128 that the counter 126 reached a count of 10 during the refractory period, the detection of noise will be declared. However, if the comparator circuit 128 determines that the counter did not reach the count of 10, the event which initiated the noise detection will be treated as a legitimate cardiac event.

Figure 4A:
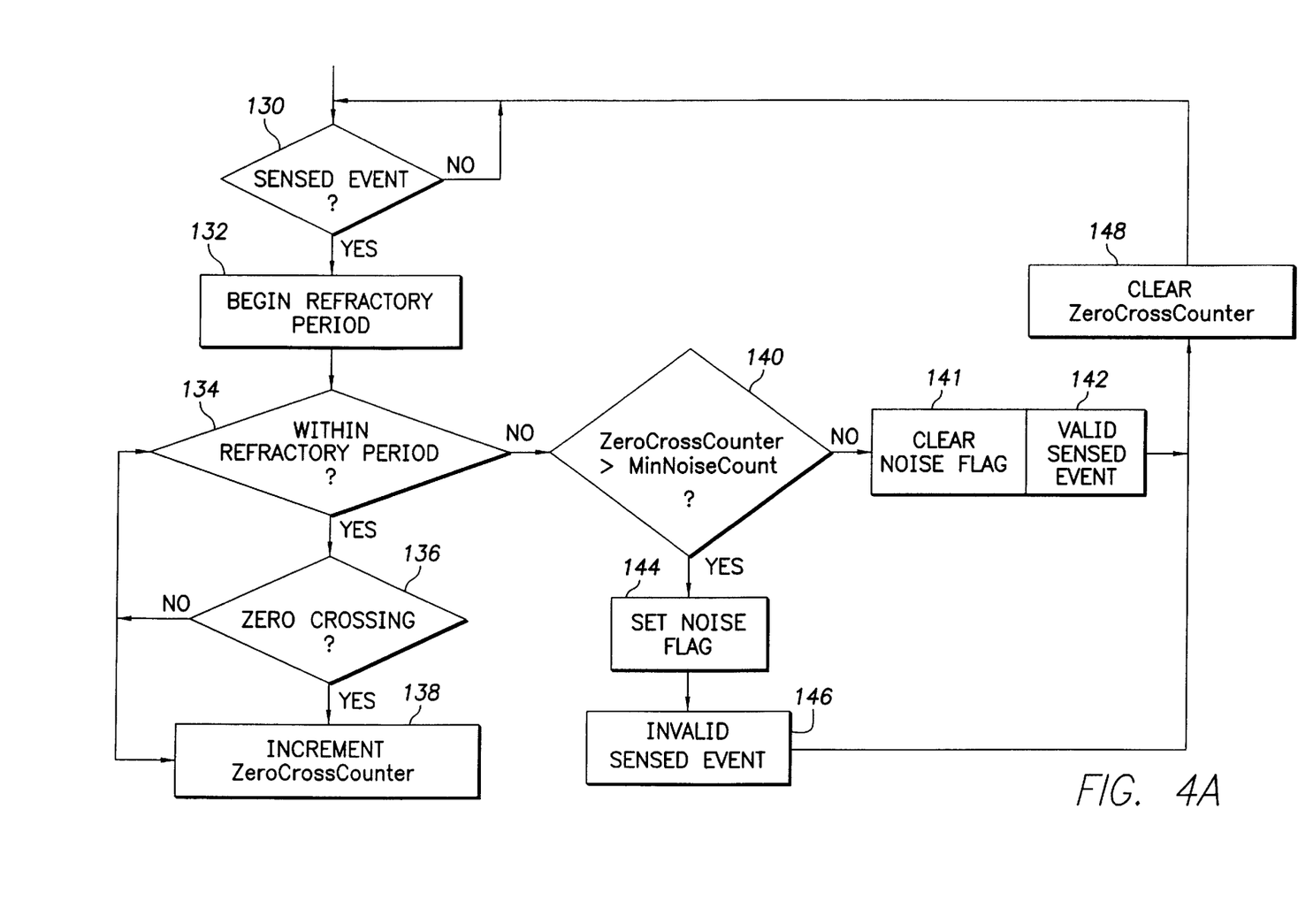
FIGS. 4A and 4B are flow diagrams illustrating the operative steps executed by the noise detection system of the present invention in accordance with preferred embodiments thereof.

FIG. 4A illustrates a flow chart of the steps which may be performed by the control/timing circuit 22 for detecting noise in accordance with one embodiment of the present invention. The noise detection mode of FIG. 4A is particularly suited for processing noise on the atrial channel. The flow chart of FIG. 4A may be read in conjunction with the exemplary atrial channel electrogram signal of FIG. 6B. The process begins at step 130 where the control/timing circuit 22 determines if the threshold detection circuit 120 sensed a cardiac event when the atrial electrogram signal 180a exceed an event threshold 182. When a cardiac event is sensed, the process proceeds to step 132 wherein the timer circuit 122 begins timing the refractory period 184. Next, in step 134, the control/timing circuit 22 queries the timer circuit 122 to determine if the implantable device is within the refractory period 184. If it is, and a zero crossing is detected in step 136 by the zero crossing detection circuit 124 (as described in reference to FIG. 5), the counter circuit (ZeroCrossCounter) 126 is then incremented in step 138. The process then returns to step 134. Steps 134, 136, and 138 are all repeated until the timer circuit 122 completes the timing of the refractory period.

Upon completion of the timing of the refractory period 184, the process then moves to step 140 wherein the comparator circuit 128 determines if the count in the counter circuit 126 is greater than the predetermined count (MinNoiseCount). If the count in the counter circuit 126 is not greater than the predetermined count, the process then proceeds to step 141 where the NoiseFlag is cleared and step 142 for the declaration of a valid sensed event. However, if the count in counter circuit 126 is determined by the comparator circuit 128 to be greater than the predetermined count, the process moves to step 144 wherein the NoiseFlag is set and step 146 where a noise event or an invalid sensed event is declared. The NoiseFlag, set in step 144, causes the control/timing circuit 22 to treat the event which initiated the noise detection as invalid and thus be treated as noise.

After step 142 or step 146 is performed, the process then proceeds to step 148 to clear the counter circuit 126. This conditions the noise detection system for the detection of noise upon the next event being detected in step 130 by the threshold detection circuit 120.

Figure 4B:
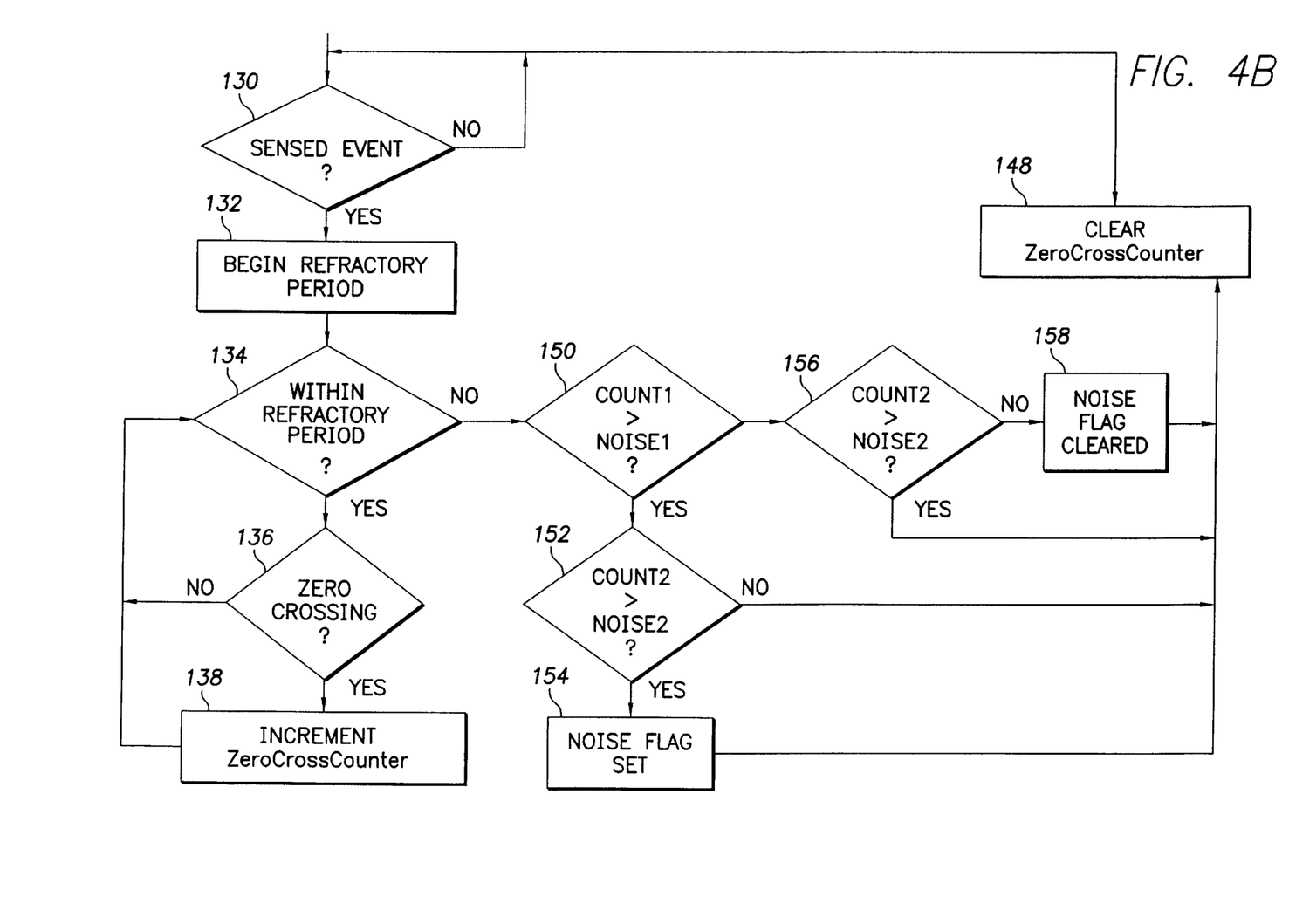
Figure 6A:
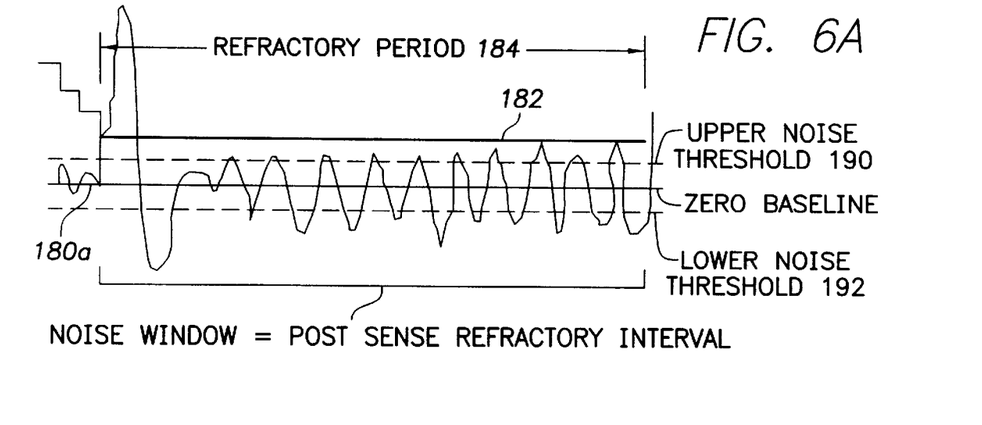
FIGS. 6A and 6B respectively show exemplary atrial and ventricle electrogram signals having noise components processed by the system of the present invention.
Figure 6B:
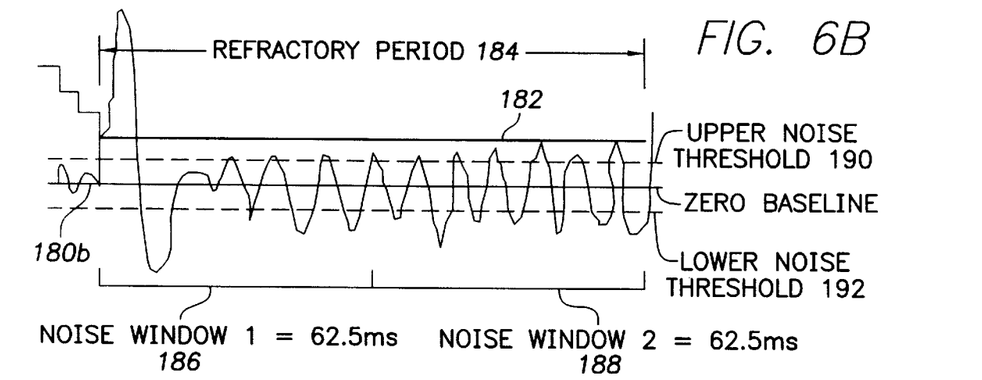

As will be appreciated by those skilled in the art, various modifications may be made to the foregoing noise detection process without departing from the present invention. For example, to render the noise detection more reliable or specific, the refractory period may be divided into multiple refractory period portions with a predetermined count assigned to each refractory portion period which must be equaled or exceeded to declare the detection of noise. For example, as processed in FIG. 4B, the refractory period 184 may be divided into first 186 (Noise Window 1) and second 186 (Noise Window 2) refractory period portions, preferably of equal durations as shown in FIG. 6B, an exemplary ventricular electrogram signal 180b. The noise detection mode of FIG. 4B is particularly suited for processing noise on the ventricular channel. In accordance with this preferred embodiment, each of the first 186 and second 188 refractory period portions would preferably have a duration of essentially one half of that shown in FIG. 4A, e.g., approximately 62.5 milliseconds. Similarly, the predetermined count for each refractory period portion would also then be preferably one half of that shown in FIG. 4A, e.g., 5 counts. Hence, after the first refractory period portion 186 is timed out, a first comparator circuit 128a determines in step 150 if the count for the first refractory period portion 186 (accumulated in counter 126a) is greater than a first predetermined amount (Noise1), e.g., 5, and if the count for the second refractory period portion 188 (accumulated in counter 126b) is also determined by second comparator circuit 128b in step 152 to be greater than a second predetermined amount (Noise2), e.g., 5, the Noise Flag is set in step 154. If the count for any one of the refractory period portions is below the associated predetermined count, the detected event initiating the noise detection will be declared and treated as a legitimate cardiac event. In a preferred implementation, if noise is also not detected in the second refractory period portion in step 156, the Noise Flag is cleared in step 158. If noise is detected in one refractory period portion, but not the other, the Noise Flag is left unchanged in the state previously determined in either step 142 or 144.

Still further, the threshold established by the threshold detection circuit for detecting an event to initiate noise detection may be either a fixed threshold or a variable threshold. Fixed thresholds are preferably used in implantable pacemakers, for example, while variable thresholds are preferably employed in implantable ICDs.

Figure 5:
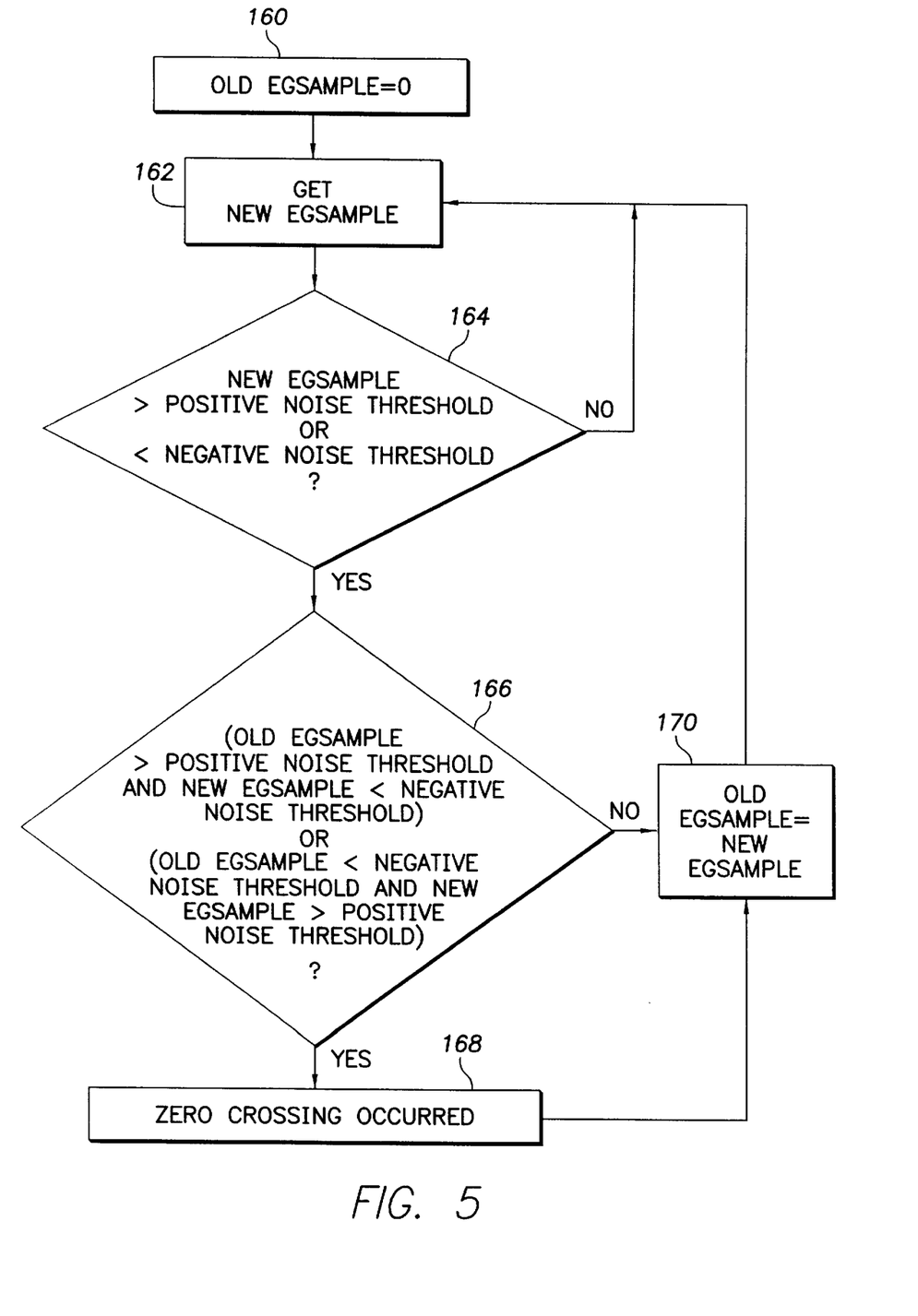
FIG. 5 is a flow diagram illustrating the manner in which zero crossings may be detected in an electrogram signal in accordance with the present invention.

FIG. 5 illustrates a flow chart of the steps that may be implemented by the zero crossing detection circuit 124 in accordance with a further embodiment of the present invention. The flow chart of FIG. 5 may be read in conjunction with the exemplary electrogram signals of FIGS. 6A and 6B. The process of FIG. 5 is initiated at step 160 by setting an old electrogram sample equal (OldEGSample) to zero. The process then proceeds to step 162 for the detection of a new electrogram sample (NewEGSample). When a new electrogram sample is detected in step 162, it is then determined in step 164 if the new electrogram sample is greater than an upper noise threshold 190 (preferably a positive value) or below a lower noise threshold 192 (preferably a negative value). If not, the process returns to step 162. However, if the new electrogram sample is above the upper noise threshold 190 or below the lower noise threshold 192, the process then proceeds to step 166 where it is determined if the magnitude of the old electrogram sample is above the upper noise threshold 190 and the new electrogram sample is below the lower noise threshold, a zero crossing is declared in step 168 by incrementing the counter circuit 126. Alternatively, if the magnitude of the old electrogram sample is below the lower noise threshold 192 and the new electrogram sample is above the upper noise threshold 190, a zero crossing is declared in step 168 by incrementing the counter circuit 126. Once the counter is incremented, the old electrogram sample is set to be equal to the new electrogram sample in step 170. The process then returns to step 162 for the detection of a new electrogram sample exceeding the event detection threshold 182.

Figure 7:
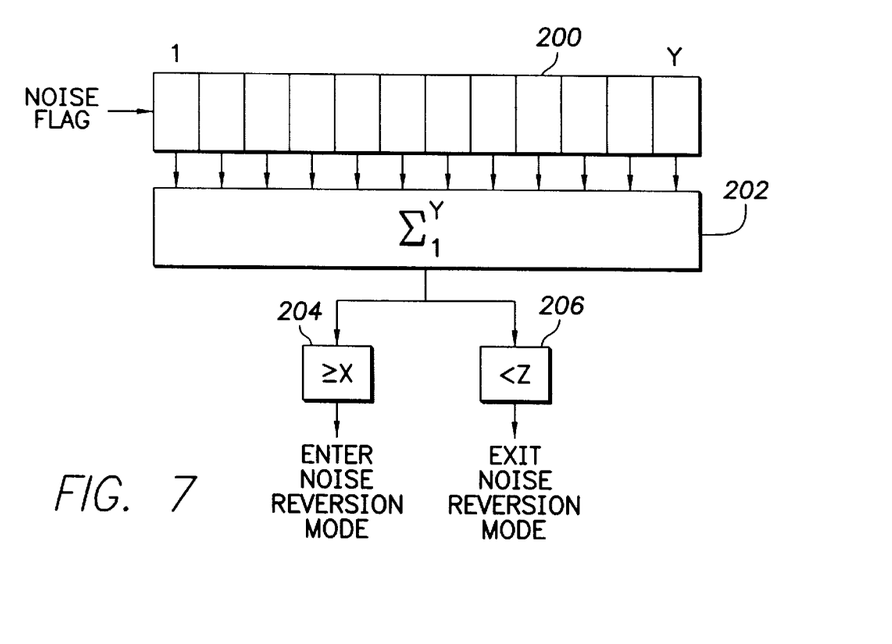
FIG. 7 is an exemplary block diagram of an apparatus (or equivalent software implementation) for determining when to enter a noise reversion mode based upon the presence or absence of a noise mode flag in a percentage of the last cardiac events.

When noise is detected in the electrogram signal, the system may enter a noise reversion mode where the system typically withholds high voltage therapy modes, e.g., in an ICD device, or enters into an asynchronous pacing mode, e.g., in a pacemaker. Preferably, the system requires more than one cardiac event (i.e., heart beats) before entering into a noise reversion mode and thus changing its operational mode. Accordingly, it is preferred that the system detect the presence or absence of noise for a percentage of the prior cardiac events before entering or exiting the noise reversion mode. For example, it is preferred that the system detect noise flags in X:Y events (i.e., X out of the last Y events, wherein X and Y are integers, for example in 8 out of the last 12 events) before changing noise reversion modes. Similarly, it is preferably that the system detect that the noise flag is cleared in Z:Y events (i.e., Z out of the last Y events, wherein Z and Y are integers, for example in 8 out of the last 12 events) before exiting the noise reversion mode. The criteria, i.e., X:Y and Z:Y, need not be the same for entering or exiting a noise reversion mode. An exemplary block diagram is shown in FIG. 7. The noise flag following each cardiac event is loaded into a FIFO 200, e.g., a shift register, which stores the last Y noise flags. A summer 202 determines the number of noise flags in the FIFO 200, i.e., the number of noise flags in the last Y events. A first comparator 204 determines if the result is greater than or equal to X (satisfying the X:Y criteria) and, if so the system enters the noise reversion mode. Conversely, a second comparator 206 determines if the result is less than a value Z (satisfying the Z:Y exit criteria) and, if so, the system exits the noise reversion mode.

While the invention has been described by means of specific embodiments and applications thereof, it is understood that numerous modifications and variations could be made thereto by those skilled in the art without departing from the spirit and scope of the invention. It is therefore to be understood that within the scope of the Claims, the invention may be practiced otherwise than as specifically described herein.

What is claimed is:

1. In an implantable medical device, a system for detecting noise in a biological signal comprising:
    a threshold circuit that generates an event signal when the signal exceeds an event threshold;
    a timer that times a time period responsive to an event signal;
    a zero crossing detector that generates a zero crossing signal when the signal transitions between upper and lower threshold values;
    a counter that counts the number of zero crossing signals during the time period;
    a comparator that compares the counter to a predetermined count; and wherein
    the biological signal is determined to be noise if the counter exceeds the predetermined count during the time period.

2. The system of claim 1, wherein the time period is a refractory period.

3. The system of claim 2, wherein the refractory period has a duration between 90 and 250 milliseconds.

4. The system of claim 1, wherein the event sensing threshold is a fixed threshold.

5. The system of claim 1, wherein the event sensing threshold is a variable threshold.

6. The system of claim 1, wherein the zero crossing detector is configured to generate a zero crossing signal when the biological signal either transitions from above an upper threshold to below a lower threshold or from below the lower threshold to above the upper threshold.

7. The system of claim 6, wherein the upper threshold is a positive value and the lower threshold is a negative value.

8. The system of claim 1, wherein the timer is configured to time a first refractory period portion and a second refractory period portion and wherein the time period is the combination of the first and second refractory period portions.

9. The system of claim 8, wherein the first and second refractory period portion have durations which are essentially equal.

10. The system of claim 8, wherein the comparator is configured to determine if the counter reached a predetermined count during each of the first and second refractory period portions.

11. The system of claim 1, wherein the system enters a noise reversion mode if the last X out of Y event signals were determined to be noise and exits a noise reversion mode when the last Z out of Y event signals were determined to not be noise, wherein X, Y and Z are integers.

12. In an implantable cardiac device, a system for detecting noise in an electrogram signal comprising:
    threshold circuit means for generating an event signal when the electrogram signal exceeds an event threshold;
    zero crossing detecting means for detecting zero crossings in the electrogram signal during a time period following an event signal;
    determining means for determining if the zero crossings detected by the zero crossing detecting means exceed a predetermined number; and wherein
    the electrogram signal is determined to be noise when the determining means determines that the detected zero crossings exceed the predetermined number during the time period.

13. The system of claim 12, further including timing means responsive to the event signals for timing the time period.

14. The system of claim 13, wherein the timing means is configured to time a first refractory period portion and a second refractory period portion and wherein the time period is the first and second refractory period portions combined.

15. The system of claim 14, wherein the first and second refractory periods have durations which are essentially equal.

16. The system of claim 14, wherein the determining means is configured to determine if the zero crossing in the electrogram signal exceed a predetermined number of zero crossings during each of the first and second refractory period portions.

17. The system of claim 12, wherein the timing period is a refractory period.

18. The system of claim 17, wherein the refractory period has a duration between 90 and 250 milliseconds.

19. The system of claim 12, wherein the event sensing threshold is a fixed threshold.

20. The system of claim 12, wherein the event sensing threshold is a variable threshold.

21. The system of claim 12, further including counting means responsive to the zero crossing detecting means for providing a count of the zero crossings in the electrogram signal during the time period.

22. The system of claim 21, wherein the determining means includes comparing means for comparing the count of zero crossings in the electrogram signal to the predetermined number.

23. The system of claim 12, wherein the zero crossing detecting means is configured to detect a zero crossing in the electrogram signal when the electrogram signal transitions from above an upper threshold to below a lower threshold or from below the lower threshold to above the upper threshold.

24. The system of claim 23, wherein the upper threshold is a positive value and the lower threshold is a negative value.

25. The system of claim 12, wherein the system enters a noise reversion mode if the last X out of Y event signals were determined to be noise and exits a noise reversion mode when the last Z out of Y event signals were determined to not be noise, wherein X, Y and Z are integers.

26. In an implantable cardiac stimulation device, a method of detecting noise in an electrogram signal comprising:
    generating an event signal when the electrogram signal exceeds an event threshold;
    detecting zero crossings in the electrogram signal during a time period following an event signal;
    determining if the zero crossings in the electrogram signal exceed a predetermined number of zero crossings during the time period; and
    identifying the event signal as noise when the determining step determines that the electrogram signal exceeded the predetermined number.

27. The method of claim 26, wherein the time period is a refractory period.

28. The method of claim 27, wherein the refractory period has a duration between 90 and 250 milliseconds.

29. The method of claim 26, further including the step of timing the time period responsive to the event signals.

30. The method of claim 29, wherein the timing step includes timing a first refractory period portion and a second refractory period portion wherein the time period is the first and second refractory period portion combined.

31. The method of claim 30, wherein the first and second refractory period portions have durations which are essentially equal.

32. The method of claim 30, wherein the determining step includes determining if the zero crossings in the electrogram signal exceed a predetermined number of zero crossings during each of the first and second refractory period portions.

33. The method of claim 26, wherein the event sensing threshold is a variable threshold.

34. The method of claim 26, wherein the event sensing threshold is a fixed threshold.

35. The method of claim 26, further including the step of counting the zero crossings in the electrogram signal during the time period to provide a count.

36. The method of claim 35, wherein the determining step includes comparing the count of zero crossings in the electrogram signal to the predetermined number.

37. The method of claim 26, wherein the detecting step includes detecting when the electrogram signal transitions from above an upper threshold to below a lower threshold or from below the lower threshold to above the upper threshold.

38. The method of claim 37, wherein the upper threshold is a positive threshold and the lower threshold is a negative threshold.

39. The method of claim 26, further including the step of entering a noise reversion mode if the last X out of Y event signals were determined to be noise and exiting a noise reversion mode when the last Z out of Y event signals were determined to not be noise, wherein X, Y and Z are integers.

40. In an implantable medical device, a system for detecting noise in a biological signal comprising:
    a timer that times a time period responsive to the biological signal, wherein the timer is configured to time a first refractory period portion and a second refractory period portion and wherein the time period is the combination of the first and second period portions;
    a zero crossing detector that generates a zero crossing signal when the signal transitions between preselected upper and lower threshold values;
    a counter that counts the number of zero crossing signals during the time period;
    a comparator that compares the counter to a predetermined count; and wherein
    the biological signal is determined to be noise if the counter exceeds the predetermined count during the time period.

41. In an implantable cardiac stimulation device, a method of detecting noise in an electrogram signal comprising:
    timing a time period that includes a first refractory period portion and a second refractory period portion wherein the time period is the combination of the first and second refractory period portions;
    detecting zero crossings in the electrogram signal occurring during the time period, said time period being initiated by the electrogram signal,
    determining if the zero crossings in the electrogram signal exceed a predetermined number of zero crossings during the time period; and
    identifying the occurrence of noise when it is determined that the number of zero crossings of the electrogram signal exceeds the predetermined number.

42. In an implantable medical device, a system for detecting noise in a biological signal comprising:
    a threshold circuit that generates an event signal when the signal exceeds an event threshold;
    a timer that times a time period responsive to an event signal;
    a zero crossing detector configured to generate a zero crossing signal when the biological signal either transitions from above an upper threshold to below a lower threshold or from below the lower threshold to above the upper threshold;
    a counter that counts the number of zero crossing signals during the time period;
    a comparator that compares the counter to a predetermined count; and wherein
    the biological signal is determined to be noise if the counter exceeds the predetermined count during the time period.

43. In an implantable cardiac stimulation device, a method of detecting noise in an electrogram signal comprising:
    generating an event signal when the electrogram signal exceeds an event threshold;
    detecting, during a time period following an event signal, when the electrogram signal transitions either from above an upper threshold to below a lower threshold or from below the lower threshold to above the upper threshold to detect a zero crossing thereby;

determining if the zero crossings in the electrogram signal exceed a predetermined number of zero crossings during the time period; and identifying the occurrence of noise when it is determined that the number of zero crossings of the electrogram signal exceeds the predetermined number.

* * * * *